United States Patent [19]

Leviness

[11] Patent Number: 5,962,537
[45] Date of Patent: *Oct. 5, 1999

[54] MULTIZONE DOWNCOMER FOR SLURRY HYDROCARBON SYNTHESES PROCESS

[75] Inventor: Stephen Claude Leviness, Baton Rouge, La.

[73] Assignee: Exxon Research and Engineering Co, Florham Park, N.J.

[ * ] Notice: This patent is subject to a terminal disclaimer.

[21] Appl. No.: 08/851,868

[22] Filed: May 6, 1997

[51] Int. Cl.⁶ .................................................. C07C 27/00
[52] U.S. Cl. ..................... 518/700; 518/706; 518/709; 518/715
[58] Field of Search ..................... 518/700, 706, 518/709, 715

[56] References Cited

U.S. PATENT DOCUMENTS

| | | | |
|---|---|---|---|
| 5,268,344 | 12/1993 | Pedrick et al. | 502/30 |
| 5,283,216 | 2/1994 | Mitchell | 502/30 |
| 5,382,748 | 1/1995 | Behrmann et al. | 585/899 |
| 5,811,469 | 9/1998 | Leviness et al. | 518/700 |

*Primary Examiner*—Gary Geist
*Assistant Examiner*—J. Parsa
*Attorney, Agent, or Firm*—Jay Simon

[57] ABSTRACT

A downcomer for producing at least two slurries having different solids and gas concentrations from a single three phase slurry of particulate solids and gas bubbles in a slurry liquid has two or more concentric gas and solids disengaging zones, each having an open fluid conduit depending from an orifice in the bottom. The dowwncomer is useful in a slurry hydrocarbon synthesis process for forming a catalyst and gas reduced slurry which is passed to a liquid filter to remove hydrocarbon liquid from the slurry reactor.

7 Claims, 3 Drawing Sheets

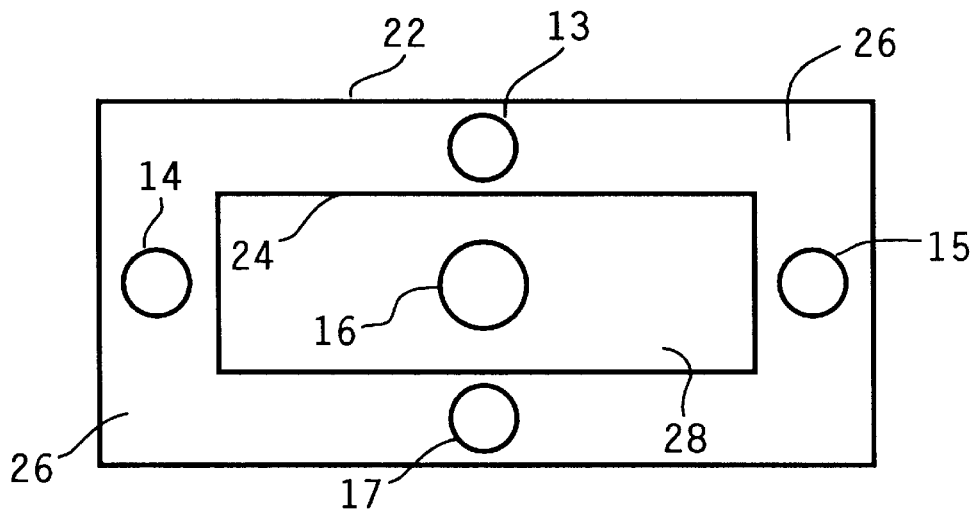
FIG. 2(b)
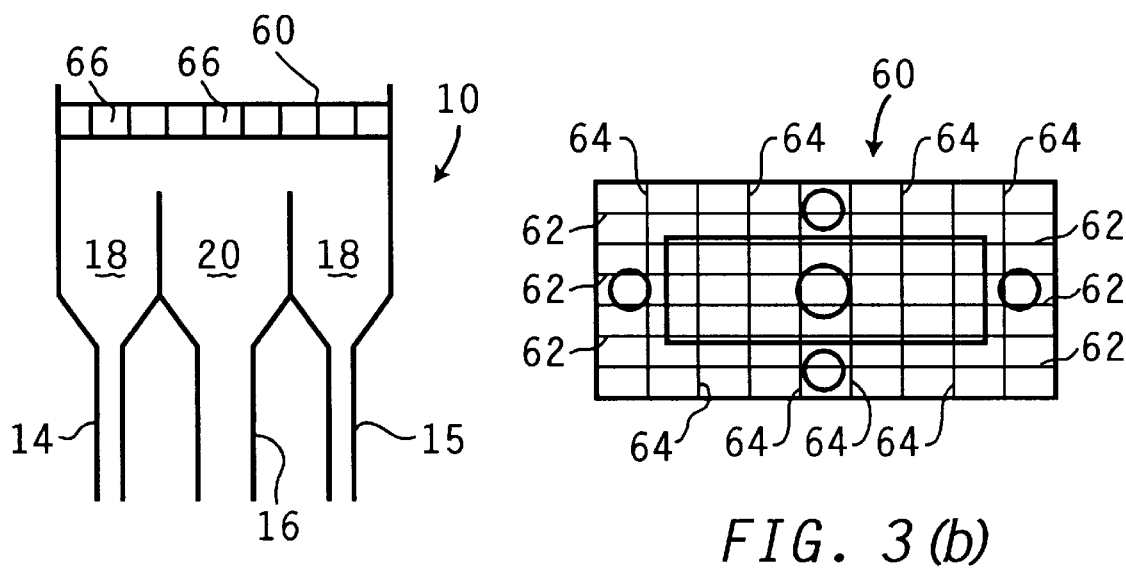
FIG. 3(a)
FIG. 3(b)

MULTIZONE DOWNCOMER FOR SLURRY HYDROCARBON SYNTHESES PROCESS

BACKGROUND OF THE INVENTION

1. Field of the Invention

The invention relates to a multizone downcomer for a three phase liquid slurry. More particularly the invention relates to a downcomer for producing at least two different solids and gas reduced slurries from a hydrocarbon synthesis slurry comprising gas bubbles and particulate solids dispersed in a hydrocarbon liquid.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical conditions of plug flow and back mixed. The catalyst particles are typically kept dispersed and suspended in the liquid by the lifting action of the syngas bubbling up through the slurry and by hydraulic means. Mechanical means such as impellers and propellers and the like are not used, because they will quickly erode and also cause attrition of the catalyst particles. One or more vertical, gas disengaging downcomers may be used as hydraulic means to assist in maintaining more uniform catalyst dispersion, by providing a vertical catalyst circulation in the slurry, as is disclosed in U.S. Pat. No. 5,382,748. The larger catalyst particles tend be more concentrated at the bottom of the slurry. It would therefore be advantageous in maintaining a more uniform vertical catalyst concentration to circulate a catalyst lean slurry to the bottom of the reactor and a catalyst rich slurry at the top. Further, the slurry liquid hydrocarbon product of the HCS reaction must be separated from the catalyst particles. This is typically accomplished by mechanical filtration in which the slurry is fed to one or more porous filter media which permit the liquid to pass through, but not the catalyst particles. The hydrocarbon liquid filtrate is then sent to further processing and upgrading. The build-up of a catalyst particle cake and plugging of the filters could be reduced if some of the catalyst particles were removed from the slurry before it is filtered. Hence, there is a need for a means of reducing the catalyst concentration in slurry being fed to the bottom of the reactor and to filtration.

SUMMARY OF THE INVENTION

The present invention relates to a means and a process for simultaneously producing slurries of two or more different compositions from a three phase slurry and is useful in a hydrocarbon synthesis (HCS) process. The slurry comprises gas bubbles and particulate solids in a slurry liquid. The means comprises two or more successive gas and solids disengaging zones, and at least one slurry transfer conduit. The process comprises passing the slurry successively through at least two gas and solids disengaging zones to form a solids and gas reduced slurry, which is then passed to a desired location by means of a fluid conduit, such as a downcomer. This invention is useful for removing gas bubbles and solid catalyst particles from an HCS slurry being fed to the bottom of the slurry body to improve vertical catalyst distribution, to slurry filtration for recovering the slurry liquid produced by the HCS reaction and also for feeding a gas reduced and catalyst increased slurry to rejuvenation. By successive zones is meant that slurry passes from the outer zone to an adjacent downstream zone and then to successively adjacent downstream zones, until it finally passes into the inner or last zone, which is furthest downstream. Adjacent zones are in fluid communication with each other, by which is meant that slurry passes from each zone into the next successive zone downstream. Gas reduced slurries may be produced which have a solids concentration both greater and less than that in the slurry body which feeds the means. As slurry successively passes from one zone to the next, adjacent downstream zone, the gas concentration in the slurry is reduced. Each zone also has downcomer means for feeding slurry from that zone to a desired location such as the top or bottom of the slurry, to filtration, to a zone or vessel external of the slurry, etc. Depending on the configuration of the zone and the means that separates it from an adjacent downstream zone, the solids concentration of the slurry fed into its downcomer may be greater than that in the slurry fed into the adjacent downstream zone. The gas and solids disengaging zones may simply be upward open cups having a respective one or more downcomers depending from the bottom, in which gas and solids are disengaged from the slurry passing through. In one embodiment, the process of the invention is achieved by means which comprises a downcomer immersed in a slurry body, with the top of the downcomer opening into a multizone gas and solids disengaging means comprising an inner zone peripherally surrounded by an outer zone and separated from the outer zone by weir means. Slurry from the slurry body surrounding the downcomer passes into the outer zone in which a portion of the gas bubbles and solids are disengaged to form two slurries which are; (i) a solids and gas reduced slurry which passes over the weir means into the inner zone, and (ii) a gas reduced and solids increased slurry which is passed out the bottom of the outer zone to a desired location. In the inner zone, additional gas is disengaged from the solids and gas reduced slurry which enters it from the outer zone, to form a gas and solids depleted slurry which is passed to and through one or more inner zone downcomer conduits to the desired location.

With particular regard to a slurry HCS process for forming hydrocarbons, at least a portion of which are liquid, the invention comprises the steps of:

(a) contacting a synthesis gas (syngas) comprising a mixture of $H_2$ and CO with a solid, particulate hydrocarbon synthesis catalyst in a slurry body comprising the catalyst and gas bubbles in a hydrocarbon slurry liquid under reaction conditions effective to form hydrocarbons from the syngas, at least a portion of which are liquid at the reaction conditions and comprise the slurry liquid;

(b) passing a portion of slurry from the slurry body into a first zone to disengage and remove a portion of the gas bubbles and form a first gas and catalyst reduced slurry;

(c) passing said first gas and solids reduced slurry into at least one adjacent zone downstream of the first zone to disengage and remove more gas bubbles in each zone and form successive gas reduced slurries, and (d) passing slurry from at least one zone into a fluid conduit by which it is passed to a desired location.

In one embodiment, solids are removed from the slurry in at least one zone, so that the slurry in the innermost or downstream zone is reduced in both gas and solids. In the embodiment referred to above in which a two zone, gas and solids disengaging means is used, a portion of the slurry body is passed into the outer zone in which a portion of the gas bubbles and solids are disengages from the slurry to form a solids and gas reduced slurry which is passed over a weir means to the inner zone, in which more gas is disengaged from the slurry to form a solids and gas reduced slurry. The solids and gas reduced slurry is then passed into and through at least one downcomer depending from at least one orifice in the bottom of the inner zone, and from there to a desired location, such as to the bottom of the slurry or to filtration means. The slurry removed from the bottom of the outer zone has less gas bubbles and more catalyst than the surrounding slurry body, and more gas bubbles and catalyst than the slurry passing out of the inner zone. In one embodiment, the outer zone and one or more bottom orifices are sized to increase the catalyst concentration in the slurry passing out of that zone into one or more downcomers. This slurry gas reduced and catalyst increased slurry may be passed to a position near the top of the slurry, where catalyst concentration is less than at the bottom, or it may be sent to means for rejuvenating the catalyst in the slurry. The slurry or slurry body from which a portion is passed into the solids and gas disengaging zones may be the reactive slurry in the HCS reactor or it may be a slurry body in an external rejuvenation or filtration zone and the fluid conduit may be a simple downcomer. Reducing the solids content of slurry sent to filtration reduces the buildup of catalyst cake on the filter and results in greater liquid throughput. During operation of the slurry solids and gas reducing downcomer, the HCS reactor may be operating or it may be shut down. If it is operating, the presence of the downcomer in the reactive HCS slurry does not disturb the HCS reaction. When the process and means of the invention is used to improve the vertical catalyst concentration in a disperse slurry reactor, the vertical temperature profile in the reactor is more uniform. This reduces hot spots and their concomitant lower selectivity to the more desired liquid hydrocarbon products. The reduction of hot spots also reduces catalyst deactivation. Catalyst deactivation increases selectivity to lower molecular weight products due to lower CO conversion. Consequently, hot spot reduction helps to maintain high CO conversion and selectivity to higher molecular weight products. A high catalyst concentration proximate the bottom of the reactor makes it more difficult to remove the exothermic heat of the HCS reaction, since the space available for heat exchangers is severely limited. This can result in the entire lower portion of the reactor running too hot, or the rest of the reactor running too cool to avoid heat build-up at the bottom. The invention reduces this by sending a catalyst reduced slurry to the bottom. While the process and means of the invention are described herein with particular reference to their usefulness in association with a slurry HCS process, the invention is not intended to be so limited. Thus, the invention may be practiced with other types of slurries and chemical processes, including biological and waste water treatment processes.

BRIEF DESCRIPTION OF THE DRAWINGS

FIGS. 2(a) and 2(b) respectively show a schematic cross-section and top view of the downcomer of FIG. 1 in greater detail.

FIGS. 3(a) and 3(b) respectively illustrate a schematic cross-section and top view of an embodiment of a disengaging means of the invention containing a slurry turbulence reducing means in the disengaging cup.

DETAILED DESCRIPTION

Figure 1:
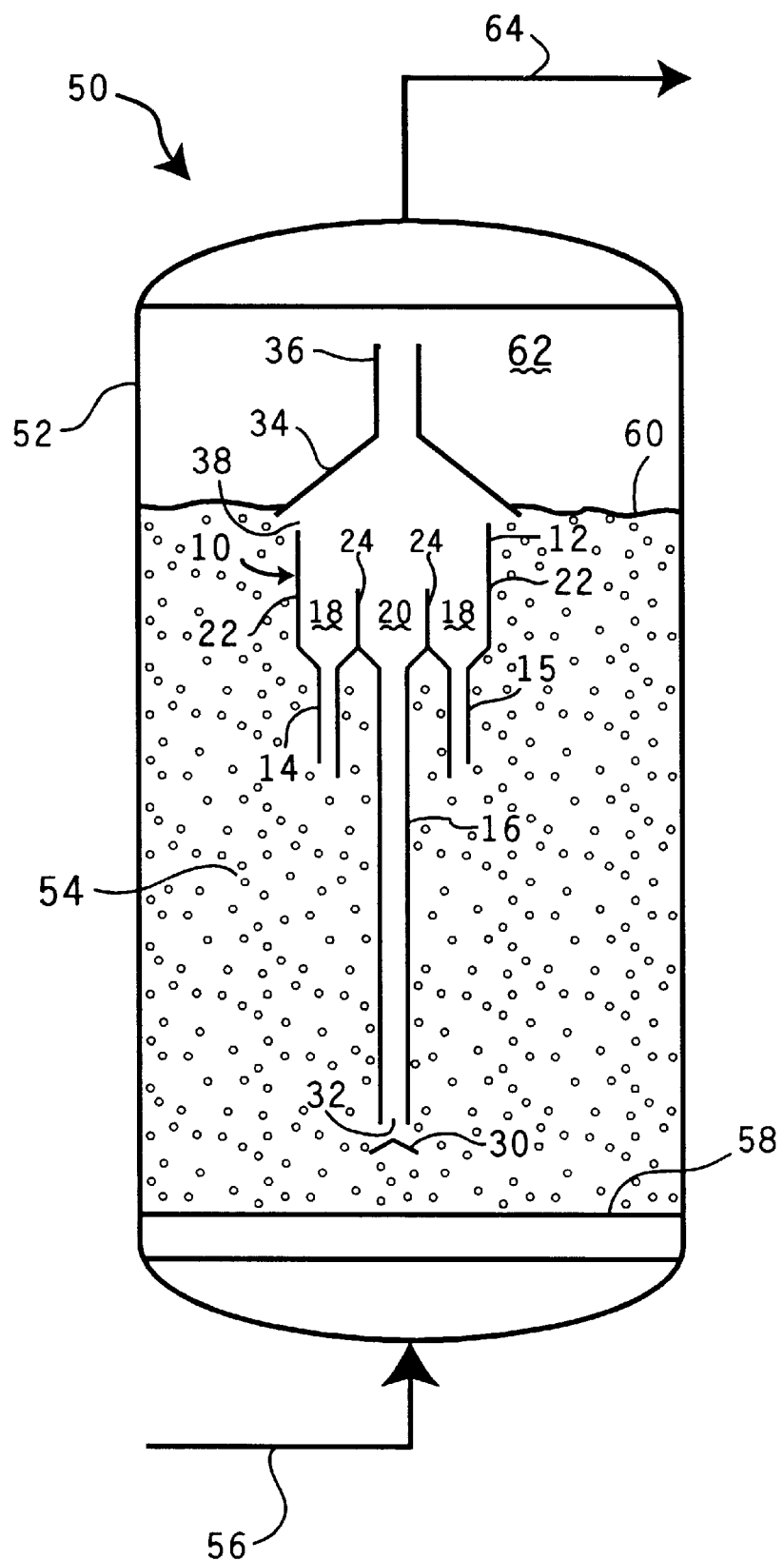
FIG. 1 schematically illustrates a schematic cross-section of a slurry type HCS reactor containing a downcomer useful in the practice of the invention.
Figure 2A:
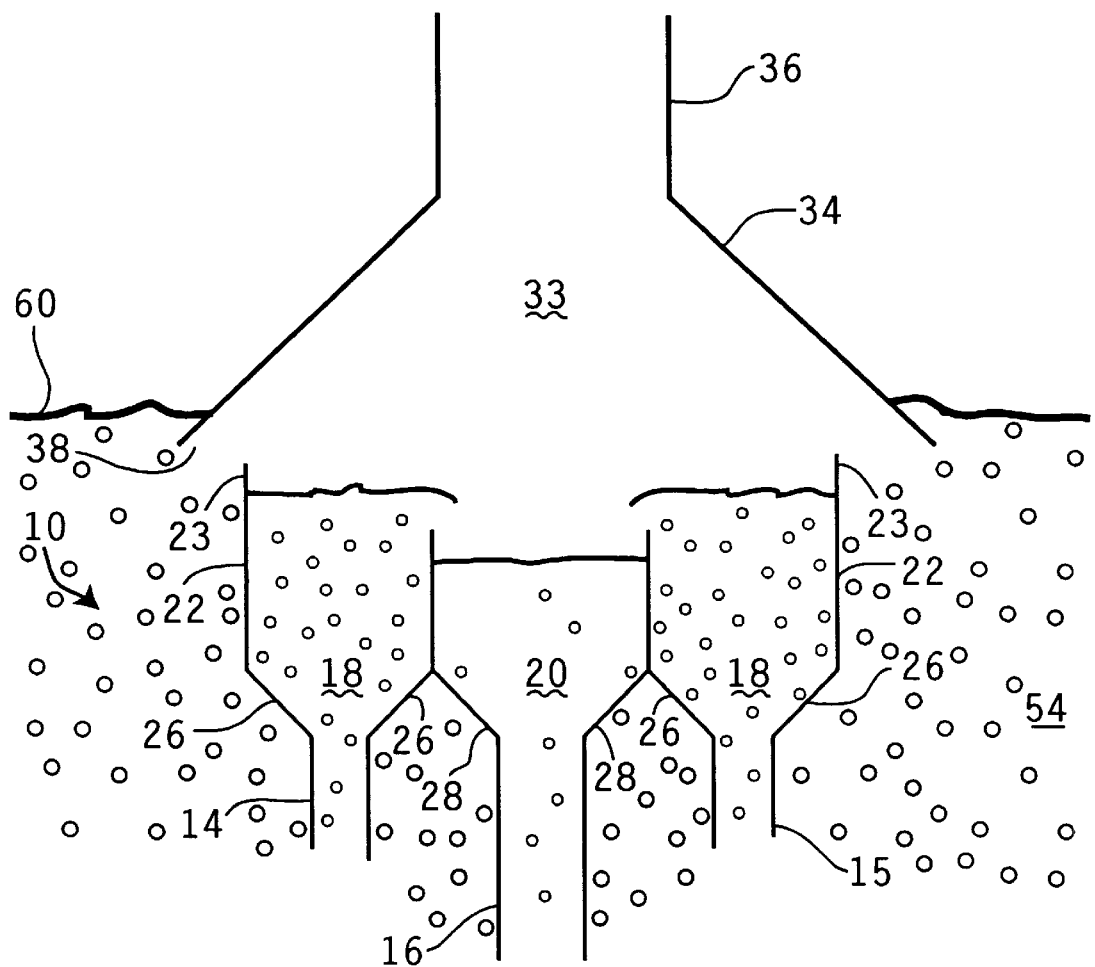

FIG. 1 schematically illustrates, in cross-section, a slurry type HCS reactor 50 comprising an outer shell 52 containing a three phase HCS slurry 54 and a downcomer 10 useful in the practice of the invention within. The slurry comprises a hydrocarbon slurry liquid in which is dispersed and suspended a particulate HCS catalyst and gas bubbles, the gas bubbles comprising syngas and HCS product gas. The slurry liquid comprises HCS reaction products which are liquid at the reaction conditions. A syngas feed inlet 56 at the bottom passes the gas up into the slurry via suitable gas distribution means arrayed across an otherwise gas and slurry impervious tray 58 located at the bottom of the slurry in the reactor. The syngas feed, which comprises a mixture of $H_2$ and CO, bubbles up through the slurry contacting the particulate catalyst to form hydrocarbon liquids, some hydrocarbon gas and water vapor. HCS reaction products which are gaseous at the reactor conditions and unused HCS syngas rise up and disengage from the top 60 of the slurry, pass up into gas disengaging and collecting zone 62, and are removed from the reactor via line 64. Not shown is filtration means, such as one or more liquid filters in the reactive slurry or in one or more filtration vessels external of the reactor. Such filtration means separate the hydrocarbon slurry liquid from the catalyst particles as filtrate, and pass the filtrate to further processing and upgrading. Magnetic means may also be used to separate the catalyst particles from the hydrocarbon liquid product if the catalyst particles are magnetic or paramagnetic, as is disclosed in the prior art. A downcomer 10 of the invention is shown as totally immersed in the slurry and comprises a gas and solids disengaging means 12 which, in this embodiment and as further illustrated in more detail in FIGS. 2(a) and 2(b), is a generally rectangular shaped cup. One or more downcomers may be employed, only one of which is shown for the sake of convenience. The interior of the gas and solids disengaging cup 12 comprises outer and inner gas and solids disengaging zones zone 18 and 20, respectively, defined by outer and inner walls 22 and 24 and inner and outer zone bottoms 26 and 28. The inner zone is peripherally surrounded by the outer zone as shown in FIG. 2(b). Zones 18 and 20 open at the bottom through respective orifices 17, 19 and 21 into respective hollow downcomer conduits or tubes 13, 14, 15, 16, and 17 which depend vertically down from the bottom of the zones. Only 14, 15 and 16 are shown in FIGS. 1, 2(a) and 3(a) for the sake of convenience. All four are shown in FIG. 2(b). Inner wall 24 also functions as a weir for gas and solids reduced slurry present in outer zone 18 to flow over and into inner zone 20, as generally illustrated by arrows 40 in FIG. 2(a). Downcomer conduits 14, 15 and 16 permit slurry in the respective outer and inner zones to flow down out of the zones to a desired location. The top of outer and inner walls 22 and 24 may be serrated or castellated to permit a smoother flow of slurry over the tops thereof. In the embodiment illustrated in FIG. 1, the slurry passing down through downcomers 14 and 15 from outer zone 18 contains a greater concentration of catalyst than both the slurry passing down through the inner zone downcomer 16 and the surrounding slurry 54. In this embodiment the length of downcomers 14 and 15 is substantially shorter than the length of downcomer 16 which extends almost to the bottom of slurry body 54, so that the slurry containing the higher concentration of catalyst is passed into the upper portion of the slurry where the catalyst concentration is normally least and the slurry containing the lower catalyst concentration is passed out the bottom of downcomer 16 proximate the bottom of the slurry where the catalyst concentration is normally the greatest, to reduce catalyst maldistribution in the slurry. A baffle in the form of, for example, a simple plate or cone 30 below the bottom opening 32 of downcomer 16, prevents feed gas from entering the downcomer without inhibiting slurry flow out of the downcomer and into the bottom of the slurry in the reactor. If syngas enters up into the downcomer it can not only inhibit and even prevent slurry flow down and out the downcomer, it can also force the slurry back up the downcomer, due to the lifting action of the gas. An inverted funnel or generally cone shaped gas and slurry baffle 34 terminating upward in gas disengaging zone 62 via a hollow chimney or gas conduit 36 is positioned over the gas disengaging means 12, with its bottom opening 38 below the top 60 of slurry body 54, to provide a slurry flow path 38 from the slurry body 54 into the outer zone 18 and a gas collecting and removal zone 33 above zones 18 and 20. FIG. 3(a) shows a further embodiment of downcomer 10 of the invention in which a slurry turbulence eliminating means 60 is positioned inside the slurry disengaging cup proximate the top thereof, for minimizing the effects of surges, splashes and other slurry turbulence in the main slurry bed that may find their way into disengaging means 12 and otherwise disturb the gas and solids release in the disengaging zones. Thus, turbulence reducer 60 aids in maintaining quiescent zones inside the disengaging cup which provides more efficient gas and catalyst disengagement. As shown in FIGS. 3(a) and 3(b), the turbulence reducing means may comprise a grid comprising a plurality of strips 62 arrayed at right angles to each other and mutually intersecting each other (not shown) in a manner similar to that of separators in a beverage carton and/or welded together, to form a plurality of open cells 66, of which only a few are labeled for the sake of convenience. These cells permit the flow of slurry down into the zones and at the same time minimize flow perturbations from disrupting the quiescence of the slurry in the zones. In another embodiment (not shown) of a downcomer of the invention similar in almost all respects to that of FIG. 1–3, the top of inner wall 24 is higher than the top of the outer wall 22 and one or more apertures or slots circumferentially present in the inner wall 24 permit slurry to flow from the outer zone 18 into the inner zone 20. These slots or apertures are located at a point below the top of the inner wall. In this embodiment, slurry cannot pass over the top of the inner wall into the inner zone. Instead, the slurry from the outer zone passes into the inner zone through the plurality of orifices or slots present in the inner wall. In this embodiment, the high inner wall acts as a barrier to slurry surges, etc. from the main slurry body in the reactor, from entering the inner zone, thereby further minimizing flow turbulence and perturbations in the inner zone which can be caused by slurry passing over the top of the inner wall and down into the slurry below in the inner zone.

Slurry entering the gas and solids disengaging means of the invention will begin to release gas bubbles as soon as it is out of contact with the gas bubbles rising up through the slurry and out of the reactor. However, surges, splashes and other slurry flow turbulence in the slurry body surrounding the gas and solids disengaging means will, if permitted to do so, cause gas and solids laden slurry from the main body to mix with the slurry in the otherwise quiescent disengaging zones. If this happens, the fresh slurry with its gas bubbles and catalyst solids will simply replace some or all of the slurry in the disengaging zones and reduce the effectiveness of the processes and disengaging means of the invention. The uprising gas bubbles in the slurry also serve to maintain the catalyst particles dispersed in the reactor slurry. However, of itself this isn't completely effective, as the vertical slurry concentration gradient known as slurry maldistribution may occur despite the uprising gas bubbles. Hence, slurry downcomers are used to reduce the slurry maldistribution as disclosed in U.S. Pat. No. 5,382,748. In operation, slurry flows into the outer disengaging zone (or, in the case of more than two disengaging zones, the first such zone) where degassing and letdown of the catalyst particles which are heavier than the liquid begins to take place. As this occurs, a gas reduced and catalyst enriched slurry is formed near the bottom of the outermost zone. This slurry exits the outermost zone via its one or more associated downcomers or other slurry transfer means at the bottom of the zone which, in the embodiments shown, pass the catalyst enriched slurry only a short distance below the top of the slurry body surrounding the means, which is where the catalyst concentration is normally least in a disperse slurry bed, rather than proximate the bottom of the reactor where the catalyst concentration is normally greatest. If desired, all or a portion of this catalyst enriched slurry in which the catalyst concentration is greater than that in the surrounding slurry body can be passed into a suitable slurry catalyst rejuvenation zone to at least partially rejuvenate the catalyst particles in the slurry. In the embodiment of FIG. 2, gas and catalyst reduced slurry in the upper portion of the outer or first disengaging zone continuously flows over the outer wall, which is a weir, and into the inner or second disengaging zone, as fresh slurry from the main slurry body continues to flow over the top of the outer wall and into the outer zone. In the inner or second zone, more gas bubbles are released from the slurry to form a gas and catalyst reduced slurry. This gas and catalyst reduced slurry passes down into the inner zone downcomer conduit and exits proximate the bottom of the slurry in the reactor where the catalyst concentration is normally least. This slurry circulation through the downcomer assists in achieving a more uniform vertical distribution of the catalyst in the slurry body.

In determining the actual sizing, shape and design of the gas and solids disengaging means of the invention, a number of factors are taken into account. The outer zone is sized to allow sufficient residence time to permit catalyst settling to the extent necessary for the catalyst reduced slurry to pass over the weir and into the inner zone, while the combined sizes of the outer and inner zones must provide sufficient slurry residence time/downward flow combination, to permit the slurry to degas to the desired extent. The cap illustrated in FIG. 2 is wide enough to cover the outer perimeter of the outer zone, with the chimney sized to allow removal of the escaping gas released from the slurry in the disengaging zones. The annular space between the inner surface of the cap and the outer perimeter of the disengaging means, or the outer perimeter of the first or outer zone, must be large enough to permit sufficient slurry flow into the disengaging means to satisfy the other requirements. Studies were made for a 3 inch downcomer of the prior art having a 2 foot diameter gas disengaging cup at the top. Immersed in an HCS slurry comprising 60 volume % gas bubbles the slurry flowing down through the downcomer would have a gas bubble concentration of only 20–40% and the hydraulic velocity of the slurry flowing down through the downcomer would be from 8–16 feet/second.

In an HCS process, liquid and gaseous hydrocarbon products are formed by contacting a syngas comprising a mixture of $H_2$ and CO with a suitable Fischer-Tropsch type HCS catalyst, under shifting or non-shifting conditions and preferably under non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlmiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonliniting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A slurry hydrocarbon synthesis proccss for forming hydrocarbons comprising:
   (a) contacting a synthesis gas comprising a mixture of $H_2$ and CO with a solid, particulate hydrocarbon synthesis catalyst in a slurry body which comprises said catalyst and gas bubbles in a slurry liquid under reaction conditions effective to from said hydrocarbons from said synthesis gas, at least a portion of which are liquid at said reaction conditions and comprise said slurry liquid;
   (b) passing a portion of slurry from said slurry body into a first zone to disengage and remove a portion of said gas bubbles and catalyst to form (i) a gas and catalyst reduced slurry from one portion of slurry in said zone and (ii) a gas reduced and catalyst increased slurry from another portion and returning said gas reduced and catalyst increased slurry back into said slurry body;
   (c) passing said first gas and solids reduced slurry into at least one adjacent zone downstream of said first zone thereby creating at least two adjacent gas disengaging zones to disengage and remove more gas bubbles in each said zone and form successive gas reduced slurries, and
   (d) passing slurry from at least one said zone into a fluid conduit by which it is passed in a desired location.

2. A process according to claim 1 wherein said catalyst and gas reduced slurry is passed to the lower portion of said slurry body.

3. A process according to claim 1 wherein said catalyst and gas reduced slurry is passed to slurry liquid filtration means.

4. A process according to claim 3 wherein said slurry is passed through more than two said zones.

5. A process according to claim 1 wherein said first zone also produces a slurry which has a catalyst concentration greater than that in said slurry body.

6. A process according to claim 1 wherein said catalyst comprises at least one supported Group VIII metal.

7. A process according to claim 2 wherein at least a portion of said hydrocarbons formed from said synthesis gas are upgraded by one or more conversion operations to at least one more valuable product.

* * * * *